United States Patent [19]

Järvelin et al.

[11] Patent Number: 5,689,013
[45] Date of Patent: Nov. 18, 1997

[54] PROCESS FOR PREPARING TERTIARY ALKYL ETHERS FROM AN OLEFINIC HYDROCARBON FEEDSTOCK

[75] Inventors: Harri Järvelin, Helsinki; Petri Lindqvist, Porvoo; Juha Jakkula, Kerava, all of Finland

[73] Assignee: Neste Ot, Espoo, Finland

[21] Appl. No.: 527,319

[22] Filed: Sep. 12, 1995

[51] Int. Cl.$^6$ .................................................... C07C 41/05
[52] U.S. Cl. .................................................. 568/697; 568/698
[58] Field of Search .................................... 568/697, 698

[56] References Cited

U.S. PATENT DOCUMENTS

| | | | |
|---|---|---|---|
| 4,724,274 | 2/1988 | Boitiaux et al. | 585/668 |
| 5,338,889 | 8/1994 | Vora et al. | 568/697 |
| 5,352,846 | 10/1994 | Sarrazin et al. | 568/697 |

FOREIGN PATENT DOCUMENTS

| | | |
|---|---|---|
| 0490571 | 6/1992 | European Pat. Off. . |
| 9319031 | 9/1993 | WIPO . |
| 9319032 | 9/1993 | WIPO . |
| 9515934 | 6/1995 | WIPO . |

*Primary Examiner*—Marianne M. Cintins
*Assistant Examiner*—Dwane C. Jones
*Attorney, Agent, or Firm*—Birch, Stewart, Kolasch & Birch, LLP

[57] ABSTRACT

The present invention concerns a process for preparing tertiary alkyl ethers. The process comprises the steps of contacting in the presence of a catalyst a feedstock containing saturated hydrocarbons and dienes having 4 to 7 carbon atoms with an excess of hydrogen in relation to the amount of dienes in the feed in order selectively to hydrogenate at least a part of the dienes, feeding the treated hydrocarbon feedstock together with at least a part of the unreacted hydrogen to a catalytic distillation reactor system which includes at least one distillation column, reacting the $C_{4-7}$ isoolefines of the feedstock with methanol or ethanol in the presence of a catalyst to form tertiary alkyl ethers, subjecting the reaction mixture to distillation in the distillation column, recovering the alkyl ethers and substantially all of the unreacted hydrocarbons with the bottoms product of the distillation, withdrawing an overhead product of the distillation, which mainly contains an azeotrope of saturated $C_4$ hydrocarbons and the alkanol, and maintaining the pressure of the distillation column at least essentially constant by adjusting the amount of gaseous distillate containing hydrogen in the column. The selective hydrogenation operation of the present invention reduces the amount of dienes contained in the feed to below 0.5% and also causes isomerization of olefins to increase the amounts of reactive olefins.

14 Claims, 2 Drawing Sheets

PROCESS FOR PREPARING TERTIARY ALKYL ETHERS FROM AN OLEFINIC HYDROCARBON FEEDSTOCK

BACKGROUND OF THE INVENTION

1. Field of the Invention

The present invention concerns a process for preparing tertiary alkyl ether products which are used, in particular, as components of motor fuels. The products contain, for example, methyl t-butyl ether, ethyl t-butyl ether, t-amyl methyl ether or t-amyl ethyl ether, or mixtures thereof, and possibly heavier tertiary alkyl ethers. According to the process, isoolefins, in particular the $C_4$–$C_7$ isoolefins, of an olefinic hydrocarbon feedstock are reacted with a suitable alkanol in order to prepare the corresponding ethers. These ethers are removed together with the bottoms product of the distillation reaction system and, if necessary, they are further processed in order to prepare a motor fuel component. Unreacted alkanol is removed with the overhead product of the distillation.

2. Description of Related Art

Tertiary alkyl ethers are added to gasoline in order to improve the anti-knocking characteristics thereof and to reduce the concentration of harmful components in the exhaust gases. The oxygen-containing ether group of these compounds has been found favourably to improve the combustion process of automotive engines. Suitable alkyl tert-alkyl ethers are methyl t-butyl ether (MTBE), ethyl t-butyl ether (ETBE), t-amyl methyl ether (TAME), t-amyl ethyl ether (TAEE) and t-hexyl methyl ether (THME), to mention a few examples. These ethers are prepared by etherification of isoolefins with monovalent aliphatic alcohols (alkanols). The reactions can be carried out in a fixed bed reactor, in a fluidized bed reactor, in a tubular reactor or in a catalytic distillation column.

The etherification reaction is an exothermic equilibrium reaction, and maximum conversion is determined by the thermodynamic equilibrium of the reaction system. To use TAME as an example, it is possible to obtain an about 90% conversion by carrying out reaction and separation in a reactive distillation column, whereas only a 65 to 70% conversion is obtainable in a fixed bed reactor.

Ion exchange resins are the most common etherification catalysts. Generally the resin used comprises a sulfonated polystyrene/divinyl benzene based cation exchange resin (sulfonated polystyrene cross-linked with divinylbenzene) having particle sizes in the range from 0.1 to 1 mm.

Two TAME processes have been commercially available for some time. The first one comprises fixed bed reactors, columns for product separation by distillation and a methanol separation unit. In the other process, the product distillation is replaced by a catalytic distillation unit, which substantially improves the TAME conversion, as mentioned above.

A third completely novel etherification process is described in our International Patent Application WO 93/19031. This novel process comprises a catalytic distillation unit which has been modified by transferring the catalyst conventionally placed in the distillation column into a separate external reactor which is being fed from the product separation distillation unit. The side reactor product is recycled back to the same product separation distillation unit. According to an embodiment of that process described in our international patent application WO 93/19032, the product distillation of the catalytic distillation reactor system is operated in such a way that most, and preferably practically all, of the alkanol which is removed with the distillate is bound to the inert $C_4$ hydrocarbons of the distillate, forming an azeotrope with them. The product is recovered from the bottom of the column and it comprises a mixture of predominantly TAME and heavier ethers.

The process described in our international patent applications mentioned above can also be used for preparing lower alkyl ethers, such as methyl t-butyl ether (MTBE) and ethyl t-butyl ether (ETBE), and mixed ether products containing such ethers.

A suitable feedstock for the above-mentioned processes for preparing tertiary alkyl ethers is Fluidized Catalytic Cracking (FCC) Gasoline containing $C_{4-7}$ hydrocarbons, a substantial portion, generally at least 5%, typically about 7 to 30 wt-%, of which comprises reactive $C_{4-7}$ isoolefins. These reactive isoolefins include the following compounds: isobutene, 2-methyl-1-butene, 2-methyl-2-butene, 2-methyl-1-pentene, 2-methyl-2-pentene, 2,3-dimethyl-1-butene, 2,3-dimethyl-2-butene, 2-ethyl-1-butene, 2-methyl-2-hexene, 2,3-dimethyl-1-pentene, 2,3-dimethyl-2-pentene, 2,4-dimethyl-1-pentene, 2-ethyl-1-pentene and 2-ethyl-2-pentene.

However, FCC gasoline also contains some 1 to 3 wt-% dienenes, such as butadiene, isoprene, pentadiene and cyclopentadiene. These dienes polymerize in the presence of ion exchange resins of the type used as catalysts in etherification processes. The polymerization of dienes results in the formation of gums which block the pores of ion exchange catalyst and decrease the activity of the catalyst. In car engines these gums are also harmful, since they cause clogging of the engine valves. Another problem associated with the diene compounds is their colour, which is not accepted in motor gasoline.

Other suitable hydrocarbon feedstocks for etherification processes are formed by Pyrolysis $C_5$ Gasoline, Thermofor Catalytic Cracking (TCC) Gasoline, Residual Catalytic Cracking (RCC) Gasoline and Coker Gasoline. These feedstocks also contain harmful diene compounds and are therefore hampered by the same problems as the FCC Gasoline.

SUMMARY OF THE INVENTION

The present invention aims at eliminating the problems associated with the prior art by providing a novel process for producing tertiary alkyl ethers from an olefinic hydrocarbon feedstock containing more than about 0.5% of dienes.

The present invention is primarily based upon the novel etherification process described in international patent applications WO 93/19031 and WO 93/19032. In particular, the hydrocarbon feedstock and at least one alkanol are fed into a catalytic distillation reactor system including at least one distillation column. In the catalytic distillation system, the components of the feed, viz., the alkanol(s) and the reactive isoolefins, are reacted with each other in order to form a product containing tertiary alkyl ethers. The reaction mixture is continuously subjected to distillation in the distillation column of the system. A bottoms product mainly containing the alkyl ethers formed and substantially all of the unreacted, unsaturated hydrocarbons is withdrawn from the distillation, whereas the overhead product mainly contains an azeotrope formed by the non-reactive (inert) feed hydrocarbons, in particular the non-reactive, saturated $C_4$ hydrocarbons, and alkanol not consumed by the etherification reaction.

According to the present invention the hydrocarbon feedstock is modified by selective hydrogenation before it is fed into the catalytic distillation reactor system. As a result of the selective hydrogenation a substantial portion of the harmful dienes contained in the olefinic hydrocarbon feedstock is eliminated and a modified hydrocarbon feedstock obtained, containing less than about 0.5 wt-% of dienes. The selective hydrogenation according to the invention is carried out in the presence of a suitable selective hydrogenation catalyst using an excess of hydrogen. Importantly, after the hydrogenation, the excess of hydrogen, i.e. the non-reacted hydrogen, is not separated from the product stream but rather conducted together with the modified hydrocarbon feedstock to the reactive distillation reactor system and used for controlling and regulating the distillation.

In particular, the process according to the present invention is mainly characterized by the following steps:

contacting in the presence of a catalyst a feedstock containing saturated and mono- and multi-unsaturated hydrocarbons having 4 to 7 carbon atoms with an excess amount of hydrogen in relation to the multi-unsaturated hydrocarbons in order selectively to hydrogenate at least a part of the multi-unsaturated hydrocarbons to form a modified hydrocarbon feedstock, the unsaturated hydrocarbons of which are primarily comprised of mono-unsaturated compounds, feeding the modified hydrocarbon feedstock together with at least a part of the unreacted hydrogen to a catalytic distillation reactor system which includes at least one distillation column, reacting the $C_{4-7}$ isoolefines of the feedstock with an alkanol in the presence of a catalyst to form tertiary alkyl ethers, subjecting the reaction mixture to distillation in the distillation column, recovering the alkyl ethers and substantially all of the unreacted hydrocarbons with the bottoms product of the distillation, withdrawing an overhead product of the distillation, which mainly contains an azeotrope of saturated $C_4$ hydrocarbons and the alkanol, and maintaining the pressure of the distillation column essentially constant by adjusting the amount of gaseous distillate containing hydrogen in the column.

BRIEF DESCRIPTION OF THE DRAWINGS

Next, the invention will be described in more detail with the aid of the attached drawings, of which

DETAILED DESCRIPTION OF THE INVENTION

Within the scope of the present application, the expression "catalytic distillation reactor system" denotes an apparatus, wherein the ether product reaction and the separation of the products take place at least partially simultaneously. The apparatus may comprise a conventional reactive distillation column or a distillation column combined with at least one side reactor. Reference is made to the embodiments described in greater detail in International Patent Applications WO 93/19031 and WO 93/19032.

The term "alkanol" includes lower alkyl alcohols capable of forming azeotropes with saturated and unsaturated hydrocarbons, in particular $C_3$ to $C_7$ hydrocarbons, of the hydrocarbon feedstock. As specific examples of the alkanols, the following can be mentioned: methanol, ethanol, n-propanol, i-propanol, n-butanol, i-butanol and t-butanol. Methanol and ethanol are particularly preferred.

Preferred "mono-unsaturated" hydrocarbons (i.e. hydrocarbons containing only one double bond) include the following, which will participate in etherification reactions: isobutene, 2-methyl-1-butene, 2-methyl-2-butene, 2-methyl-1-pentene, 2-methyl-2-pentene, 2,3-dimethyl-1-butene, 2,3-dimethyl-2-butene, 2-ethyl-1-butene, 2-methyl-2-hexene, 2,3-dimethyl-1-pentene, 2,3-dimethyl-2-pentene, 2,4-dimethyl-1-pentene, 2-ethyl-1-pentene, 2-ethyl-2-pentene, and 1-methyl-cyclopentene.

The "multi-unsaturated" hydrocarbons discussed in the present context are primarily represented by butadiene, pentadienes (such as isoprene) and cyclopentadiene and dienes having 6 or more carbon atoms. The selective hydrogenation of isoprene and similar higher dienes containing a methyl side group is particularly important as it will produce isoolefins which can be etherified. Also acetylenic compounds such as butynes, in particular 2-butyne, pentynes and hexynes are present in the olefinic hydrocarbon feedstocks. They will yield mono-unsaturated hydrocarbons upon hydrogenation.

The term "olefinic hydrocarbon feedstock", is intended to cover all hydrocarbon feedstocks, which contain a mixture of isoolefins which can be etherified to form tertiary alkyl ethers. In particular, the following feedstocks are preferred: FCC Gasoline, FCC Light Gasoline, Pyrolysis $C_5$ Gasoline, TCC Gasoline, RCC and Coker Gasoline. The feed can also comprise a mixture of two or more olefinic hydrocarbon feedstocks, such as a mixture of FCC Light Gasoline and a pyrolysis $C_5$ cut. The proportion of the various $C_4$ to $C_7$ isoolefins will, of course, to a large extent determine the composition of the ether product.

Of the above feedstocks, FCC, RCC and TCC are preferred because these hydrocarbon cuts can be used as such, possibly after the removal of heavier cuts ($C_{8+}$). The use of Pyrolysis Gasoline requires that the light cut and the $C_{6+}$ cut be removed before it can be fed into the hydrogenation unit. In particular, it is important to remove all aromatic compounds. Up to some 10% of the $C_{6+}$ cut can be included in the resulting hydrocarbon mixture, called a Pyrolysis $C_5$ Gasoline, so as to ensure that substantially all of the reactive $C_5$'s of the Pyrolysis Gasoline are present in the olefinic feedstock. This feedstock will also contain reactive aliphatic $C_{6+}$ hydrocarbons. Pyrolysis Gasoline is particularly rich in isoprene (up to 10 wt-%) and the selective hydrogenation according to the present invention will greatly improve the value of this cut as a feedstock for etherification, in particular in combination with any of the above mentioned cracking gasoline cuts.

It is known in the art (cf., for example, U.S. Pat. Nos. 4,724,274 and 5,352,846) selectively to hydrogenate dienes of pure $C_5$-cuts. These cuts are chemically rather uniform and the molecular weights of the hydrocarbons contained therein are of the same magnitude. In contrast, according to the present invention, the olefinic hydrocarbon feedstock which is to be hydrogenated contains a complex mixture of a broad range of $C_4$ to $C_7$ hydrocarbons. These mixtures include tens of different aliphatic dienes, which can be straight- and branched-chained, as well as cyclic. As an example of the last mentioned species, the olefinic naphthenes should be mentioned. It is therefore surprising that the conventional hydrogenation catalysts used in the present invention are capable of achieving selective hydrogenation of all the different dienes present in mixtures of $C_4$ to $C_7$ hydrocarbons, bringing the diene content to below 0.1 wt-%. The more reactive the diene is, the more easily it is hydrogenated. In the following, hydrogenation carried out in according with the invention, is called "selective hydrogenation", indicating that it preferentially affects the multi-unsaturated compounds contained in the hydrocarbon feedstock converting them to mono-unsaturated compounds, although some minor amounts of mono-unsaturated components originally contained in the feed may become saturated.

The hydrogenation process of the present invention does not only achieve selective hydrogenation of the feed, it also isomerizes the olefin compounds. The reactive components in the etherification are tertiary olefins. Of the tertiary olefines the alfa-olefins, in which the double bond is nearer the end of the molecule, are more reactive than the beta-olefins. As far as etherification of an olefinic feedstock containing a mixture of reactive olefins is concerned, it is very important to maximize the amount of formed alfa-olefins. Surprisingly, it has turned out that the present selective hydrogenation process also isomerizes some non-reactive components, like 3-methyl-1-butene and isoprene, to reactive components, like 2-methyl-1-butene and 2-methyl-2-butene. This isomerization considerably increases the profitability of the etherification.

Hydrogenation produces a modified hydrocarbon feedstock, at least about 80%, preferably at least about 90% and in particular at least about 99.9% of the unsaturated hydrocarbons of which are comprised of mono-unsaturated compounds. Of the multi-unsaturated hydrocarbons at least about 80%, preferably at least about 90% are then hydrogenated during the selective hydrogenation operation.

Figure 1:
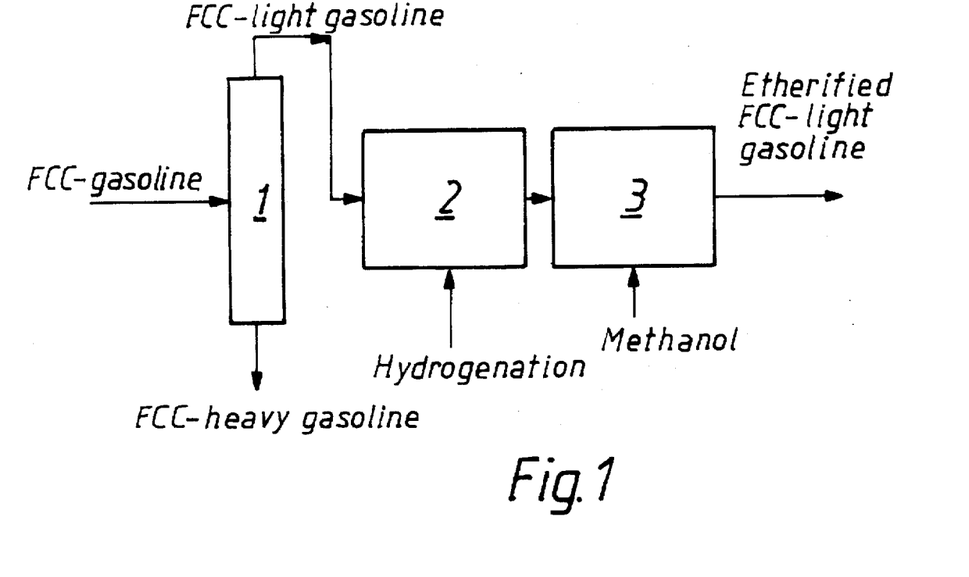
FIG. 1 depicts a simplified scheme of the TAME process according to the present invention, comprising a FCC gasoline splitter, a selective hydrogenation unit and an etherification unit.

FIG. 1 gives an overview of the process according to the present invention. Thus, in the present etherification process an olefinic hydrocarbon feedstock, for instance an FCC Gasoline, optionally after removal of the heavy fraction in an FCC gasoline splitter 1 to produce an FCC Light Gasoline, is conducted to a selective hydrogenation unit 2 to form a modified hydrocarbon feedstock containing only small amounts of diene compounds, if any. The modified feedstock containing $C_{4-7}$ hydrocarbons is mixed with a suitable alkanol and fed into a etherification unit 3 comprising a catalytic distillation reactor system. In the etherification unit, the $C_{4-7}$ isoolefins of the feedstock react with the alkanol in the presence of a cation exchange resin to form tertiary alkyl ethers. The alkyl ethers are removed from the distillation reactor system with the bottom product and, if desired, subjected to further processing in order to produce an etherified gasoline product. Most of the unreacted hydrocarbons (except for the $C_4$'s) are also removed with the bottoms product of the distillation.

According to a preferred embodiment, the selective hydrogenation unit consists of two sequentially arranged reactors. As far as the basic concept of the invention is concerned, satisfactory results are obtained already with one hydrogenation reactor. However, two or more reactors are preferred to ensure that the operation cycle becomes long enough. Thus, when the catalyst in the first selective hydrogenation reactor is deactivated, the second reactor can be used, and the production can be continued. The cost of a reaction vessel together with necessary instruments is minor to the cost of production losses. Furthermore, the use of two reactors will reduce the amount of catalyst needed, because only the operative reactor needs to be filled with catalyst. If one big reactor is used, most of the catalyst is superfluous during the initial stage of the operation and therefore causes unnecessary costs.

Figure 2:
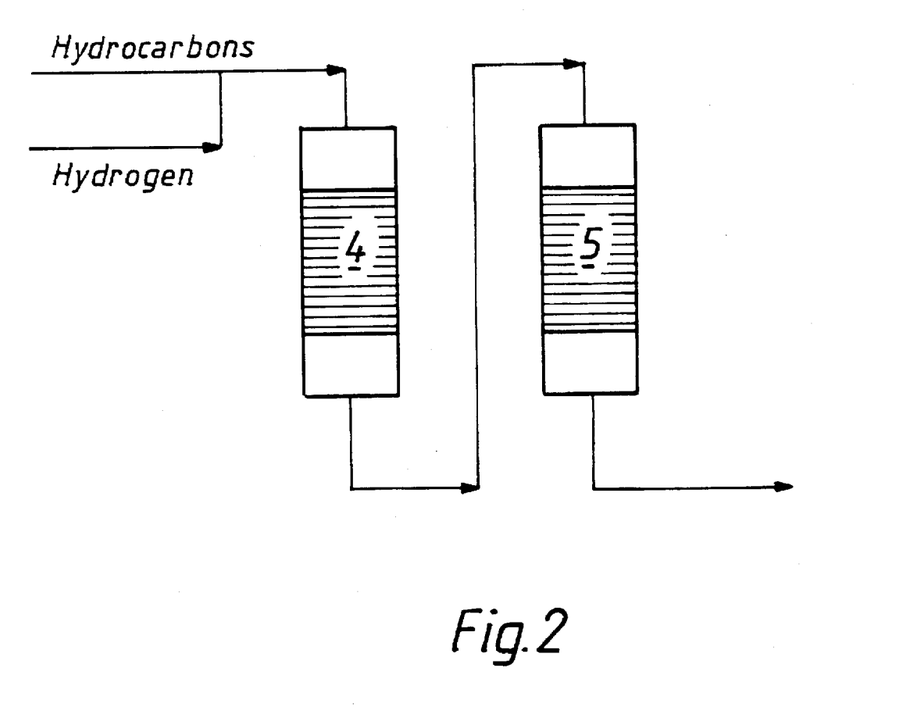
FIG. 2 depicts a simplified scheme of a selective hydrogenation unit used in the present invention, and FIG. 3 gives a schematic depiction of the etherification unit comprising three prereactors, a product separation column, and two side reactors.

FIG. 2 illustrates the preferred configuration of the selective hydrogenation unit, including a first hydrogenation reactor 4 and a second hydrogenation reactor 5. The hydrocarbon feedstock and hydrogen gas are combined before the first reactor and conducted under pressure to the hydrogenation unit. The feed conduit can be provided with a static mixer in order to promote the mixing of the gaseous hydrogen into the liquid hydrocarbon feed. Dissolution of the hydrogen in the hydrocarbon phase and hydrogenation of the dienes is promoted by having the hydrogen dispersed throughout the hydrocarbon feed in the form of minute bubbles.

The hydrogen used for hydrogenation can be comprised of hydrogen gas of any suitable purity (typically 10–100 wt-%). The gas can contain 0 to about 90 wt-%, preferably 10 to 70 wt-% of other volatile components, such as hydrocarbons, which remain inert both during selective hydrogenation and etherification. These kinds of hydrocarbons can be used along with the excess hydrogen for controlling the pressure of the column. Example 1 shows the use of hydrogen gas containing up to about 50 to 60 wt-% of methane and other light paraffinic hydrocarbons.

The selective hydrogenation is operated at a pressure in the range of 10 to 120 bar, preferably at 15 to 115 bar, in particular at about 20 to about 40 bar, in order to keep the hydrogen in the liquid phase. It is preferred to have a substantial portion, suitably at least about 80%, and preferably at least 90%, of the hydrogen dissolved in the hydrocarbon feedstock during hydrogenation.

Hydrogen is fed at a molar ratio of some 1.001 to 10 times, preferably about 1.05 to 2 times the amount of dienes present in the feed. When calculating the molar amounts of dienes, any acetylenic hydrocarbons should also be included. In order to limit hydrocarbon losses during pressure regulation in the column (cf. below), a moderate excess of hydrogen is preferred. Therefore, the above-mentioned preferred range, corresponding to a hydrogen excess of 1 to 1000 mol-% in relation to the dienes of the hydrocarbon feedstock, is suitable. An excess of 5 to 200 mol-%, for instance 10 to 40 mol-%, is particularly preferred.

After the hydrogenation, the excess hydrogen is fed into the etherification reactor unit. According to one preferred embodiment all of the unreacted hydrogen, i.e. essentially all of the excess hydrogen used for hydrogenation, is conducted with the selectively hydrogenated hydrocarbon feedstock to the etherification unit. By conducting all of the excess hydrogen to the etherification, there is no need for any separate hydrogen removal equipment. However, if desired, it is also possible to remove some, for instance 10 to 90%, of the unreacted hydrogen prior to etherification.

The catalysts for the selective hydrogenation according to the invention preferably comprise supported noble metal (Group VIII) hydrogenation catalysts. Nickel-based catalysts can also be used. The metals of the catalysts include Pd, Pt, Re, Rh, Ag and Au and mixtures thereof. The supports of the catalysts typically consist of inorganic metal oxides, such as alumina and silica. Particularly suitable catalysts are represented by commercial, heterogeneous palladium-based hydrogenation catalysts. The amount of palladium is normally 0.2 to 5 wt-% calculated on the total weight of the catalyst. The support consists of alumina.

If necessary to modify the action of the catalyst, a small amount of sulfur can be added during hydrogenation. In this case, a sulfur compound is used in an amount of 1 to 100 ppm calculated on basis of the hydrocarbon charge.

The temperature of the hydrogenation is in the range from about 20° to 300° C. The temperature depends on pressure, catalyst and hydrogen-to-hydrocarbons -ratio. According to a preferred embodiment, the temperature is increased in the range from about 40° C. to about 130° C. during operation in order to compensate for the deactivation of the catalyst. Thus, at a pressure of some 20 to 40 bars, using a supported palladium catalyst, and working with an excess of hydrogen of more than 10%, the initial temperature can be set at 70° to 80° C. and the final temperature at 120° to 130° C.

According to a preferred embodiment of the present invention an excess of at least 5 mol-% (for example, 10 to 15 mol-%) of hydrogen is fed into the hydrogenation process and the pressure of the hydrogenation process is kept at 15 bar or higher. In this case, the pressure of the distillation is kept at 10 bar or lower.

Figure 3:
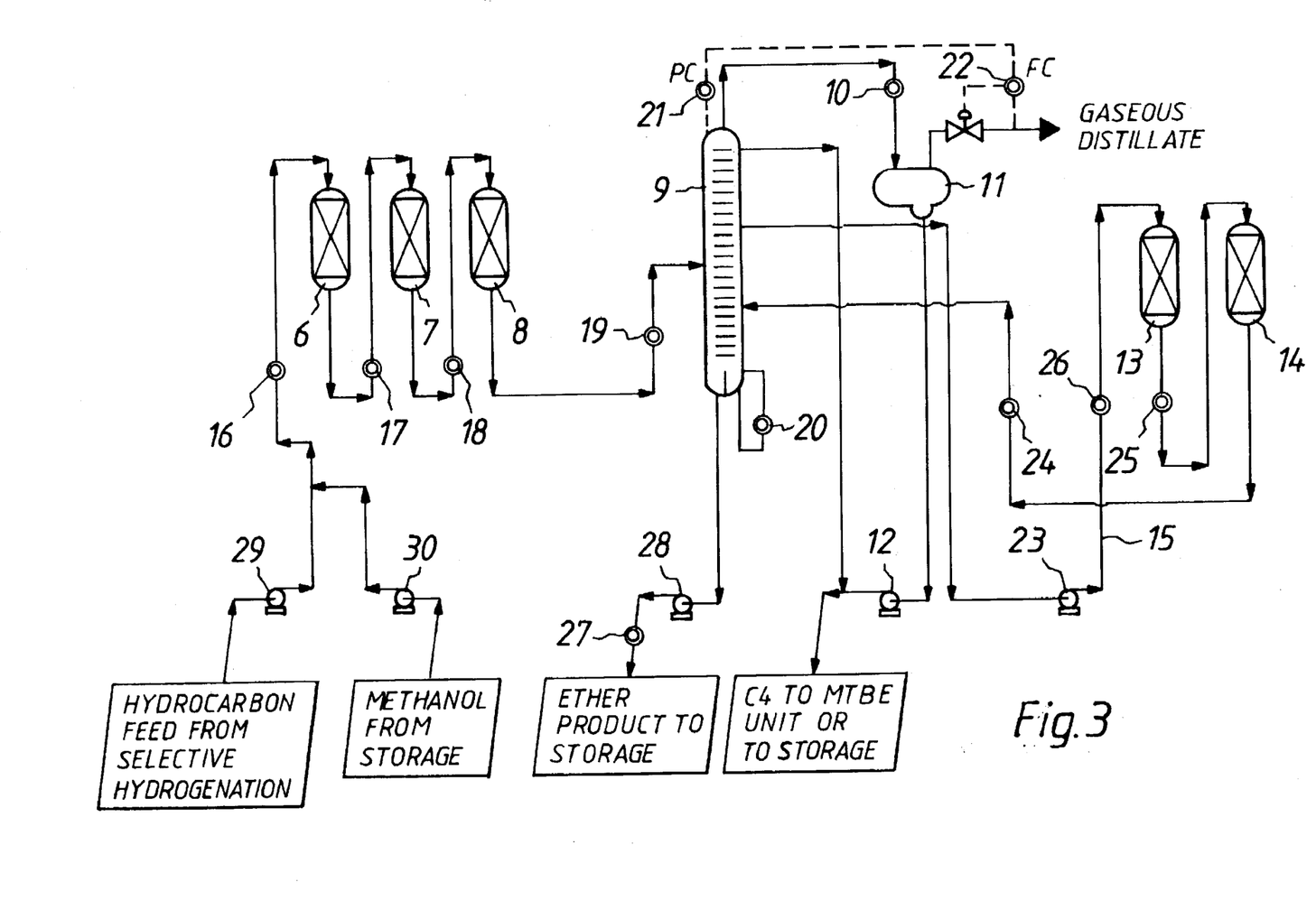

FIG. 3 depicts a simplified scheme of the TAME process described in the working examples.

The selectively hydrogenated hydrocarbon feedstock and the methanol needed for the etherification are fed under pressure (pumps 29, 30) and mixed together, the mixture is heated or cooled to obtain a proper feed temperature and then the mixture is fed through prereactors 6, 7 and 8. It should be noticed that, according to the invention, it is possible to feed the alkanol either into the hydrocarbon feedstock or into the side stream entering the side reactors (cf. below) or as a combination of these two alternatives. The prereactors consist of three reactors filled with ion exchange resin. The reactors can be fixed or fluidized bed or tubular reactors. The reactors may be arranged in series, as shown in the figure, or in parallel. If there are more than two prereactors they may also be arranged in series/parallel. Because of the reaction there is a temperature rise in the prereactors in the range from about 5° to about 15° C. depending on the efficiency of the reactor insulation. Heat-exchangers 16–18 are arranged before the prereactors 6–8 in order to cool or heat the fluid streams to desired temperature.

From the prereactors the mixture is conducted via a further heat-exchanger 19 to distillation column 9, which in the following is also called the main fractionator. The distillation column can be a packed column or one provided with valve, sieve or bubble-cap trays. At the bottom of the column there is fitted a reboiler 20. The overhead of the column is removed via a condenser 10 to a reflux drum 11, from which the overhead is removed by means of a pump 12. A part of the overhead is forwarded to further processing, for instance to a MTBE process, and a part thereof is returned to the column. TAME and heavier ethers are removed with the bottoms product by using a pump 28 and, if desired, cooled 27 before being conducted to storage. In addition to the ethers, the bottom product also contains unreacted $C_{5+}$ hydrocarbons.

The reflux ratio of the column is preferably from about ½ to 200. Even greater ratios can be used in pilot plant equipments. According to the invention, the reflux ratio is adjusted so that the distillate amount removed from the process substantially corresponds to the amount of $C_4$ hydrocarbons and other inert feed hydrocarbons which form an azeotrope with the alkanol used for etherification. The top of the column is provided with pressure control means 21, which is operably connected to a flow control means 22, which regulates the amount of gaseous distillate removed from the reflux drum 11.

Next to the distillation column 9 a side reactor system has been arranged, which consists of two reactors 13, 14 in series. The reactors can, if desired, be replaced by one larger reactor. The side stream flow can be effected as a forced circulation by using a pump or by thermosyphon. Depending on the mode of circulation the reactors can be fixed or fluidized bed reactors or tubular reactors, as mentioned above in the general part of the description. The side reactors are fed with a liquid stream taken from the column. The pressure of the liquid stream can be increased by a pump 23. The side stream is preferably taken from a tray which is located below trays having methanol K-values less than 1. Additional methanol can, if needed, be fed to the side reactor feed before the side reactor (point 15). The reactor feed can be cooled by a heat-exchanger 24 to the reaction temperature before the side reactor. The temperature rises only by a few degrees in the side reactors. The temperature of the liquid stream from the first and the second reactors, respectively, can be adjusted by heat-exchangers 25, 26. From the side reactor system 13, 14 the liquid flow is routed back to column 9. It is then returned to a plate having a methanol K-value greater than 1.

The reactor effluent enters the column typically at a location below the feed coming from the prereactors 6–8. The aim of this arrangement is to make the column 9 operate in such a manner that the methanol in the overhead product is bound to the $C_4$ hydrocarbons in the form of an azeotrope.

Other alkanol ethers, such as MTBE, ETBE and TAEE can be prepared in a similar manner.

The distillation is carried out at a substantially lower pressure than the selective hydrogenation, the distillation pressure generally ranging from about 1.1 to 10 bars. Therefore, the volatile components of the feed stream will at least partially evaporate once they enter the distillation column 9. Normally, some 50 to 100% of the dissolved hydrogen will evaporate upon entry into the column.

When preparing TAME, the temperature at the top of the distillation column is about 40° to 70° C., typically about 50° to 60° C., and at the bottom of the column about 100 to 150, typically about 120° to 130° C.

As mentioned above, according to the present invention the distillation column of the reactive distillation unit is operated in such a way that the alkanol is heavier than the hydrocarbons at the top of the distillation column. Therefore, the alkanol not bound to the hydrocarbons in the form of an azeotrope will tend to flow downwards within the column. At the same time the vapor-liquid-equilibrium between $C_5$ and heavier hydrocarbons and the alkanol at the bottom of the column is maintained at such a level that the alkanol is lighter than the hydrocarbons. This causes the alkanol to flow upwards from the bottom of the column. Thus, the alkanol will circulate within the distillation system between the top and the bottom of the column. By fitting a reaction bed in the distillation column or by conducting a side stream from the column through a reaction bed in a side reactor, an alkanol consuming reaction can be created which will remove the alkanol from the system.

The alkanols, in particular methanol and ethanol, form azeotropes with the hydrocarbons of the feedstock. The heavier the hydrocarbons, the greater the alkanol concentration of the hydrocarbon-alkanol-azeotrope. According to the present invention, in order to minimize the amount of unreacted alkanol removed from the distillation process, substantially only the $C_4$-hydrocarbon-alkanol azeotropes are taken as an overhead product. These azeotropes are the lightest hydrocarbon-alkanol azeotropes and have the smallest alkanol concentrations.

Thus, according to the present invention, the amount of unreacted alkanol can be controlled by adjusting the amount of $C_4$ hydrocarbons in the feed so that it correlates with the amount of alkanol. The less there are $C_4$ hydrocarbons in the feed, the less distillate can be removed and the less alkanol is removed from the process. By increasing the amount of $C_4$ hydrocarbons in the feed the distillate flow rate can be increased without any change of the relative amount of free unreacted alkanol in the overhead product. Therefore, if desired, $C_4$ hydrocarbons (or even $C_3$ hydrocarbons) can deliberately be added to the process so that the intended effect is achieved.

In the main fractionator 9, light hydrocarbons and excess hydrogen are taken as vapour distillate together with some stripped $C_4$-hydrocarbons and methanol. This stream is used to control the pressure of the main fractionator. If there were no vapour flow, the pressure control of the main fractionator would be difficult, because the distillate flow is normally very small compared to the reflux flow (the reflux ratio is usually over 100). It is not possible to use the distillate flow for any fast control purpose. However, according to the present invention, by regulating the amount of gas distillate by means of a pressure valve and by keeping the pressure at least approximately constant, distillation can be operated under stable conditions. The withdrawn hydrogen and methane together with any hydrocarbon azeotrope and other hydrocarbon atoms can be recirculated to hydrogen recovery. Preferably the compounds are conducted to a flue gas system.

When operating the process according to the invention, the alkanol concentration of the bottoms product of the column can easily be reduced to as small a value as desired. In the case of methanol, it is possible to reduce its concentration in the bottoms product to below 100 ppm. The amount of alkanol in the distillate will correspond to the amount bound by the azeotrope, only. The composition of the azeotrope and, thus, the amount of alkanol removed depends on the hydrocarbon composition of the overhead product and the operating pressure of the distillation. To mention an example based on the production of TAME: if $C_4$ hydrocarbons make up the main part (over 90%) of the overhead product, there will remain some 0.1 to 5.0% by weight of methanol depending on the distillation pressure and the amount of $C_5$ hydrocarbons. The more $C_5$ hydrocarbons are included in the overhead product, the more methanol will be removed with it (there may be less than 90% by weight of the $C_4$ hydrocarbons in the overhead product).

The above-described etherification is preferably carried out in the presence of a conventional cation exchange resin. However also different kinds of zeolites can also be used as etherification catalysts. Thus, the resin may contain sulfonic acid groups and it can be obtained by polymerization or copolymerization of aromatic vinyl compounds followed by sulfonation. Examples of aromatic vinyl compounds suitable for preparing polymers of copolymers are: styrene, vinyl toluene, vinyl naphthalene, vinyl ethylbenzene, methyl styrene, vinyl chlorobenzene and vinyl xylene. The acid cation exchange resin typically contain some 1.3 to 1.9 sulfonic acid groups per aromatic nucleus. Preferred resins are based on copolymers of aromatic monovinyl compounds with aromatic polyvinyl compounds, particularly, divinyl compounds, in which the polyvinyl benzene content is from about 1 to 20 wt-% of the copolymer. The ion exchange resin preferably has a granular size of about 0.15 to 1 mm.

In addition to the above resins, perfluorosulfonic acid resins which are copolymers of sulfonyl fluorovinyl ethyl and fluorocarbon can be used.

According to a preferred embodiment the location of the drawoff from the column to the side reactor is selected in such a way that the vapour-liquid equilibrium ratio (the K-value) of the alkanol is smaller than 1 on the (theoretical) trays above it. If TAME is prepared, the process can be operated in such a way that the K-value of the methanol is smaller than 1 on the trays above the drawoff tray. In the TAEE process, there is (are) usually 1 or 2 (theoretical) tray(s) between the drawoff tray and the first tray above it which has a K-value for ethanol smaller than 1. The reaction product containing the alkanol is returned from the side reactor to the column and it is fed to a tray having an alkanol K-value greater than 1. As a result the alkanol gets more enriched in the vapor phase than do the hydrocarbons. The side stream makes up 40 to 90%, typically about from 60 to about 70% of the total liquid flow within the column. The use of a side reactor is preferred, e.g., for the reasons that the conditions prevailing in the distillation column can be influenced by changing the drawoff location of the side stream and by feeding more alkanol to the reaction bed.

The invention can also be applied to a conventional catalytic distillation reactor. It is operated in the same way as a side reactor process. The only difference is that the alkanol consuming reaction takes place within the column.

The invention is preferably carried out in connection with the MTBE, ETBE, TAME and the TAEE processes.

In connection with the TAME process, the overhead product obtained can be forwarded to a MTBE unit. Since it contains some impurities ($C_5$ hydrocarbons, as far as the MTBE process is concerned), the overhead product can be introduced either in the feed of the MTBE unit, which means that the $C_5$ hydrocarbons remain in the MTBE product, or to the methanol washing unit of the MTBE unit. In the latter case the $C_5$ hydrocarbons end up in the raffinate stream of the MTBE unit (which contains mainly $C_4$ hydrocarbons).

Alternatively, the overhead product of the distillation can—because it contains only minute amounts of methanol and because the overhead is very small compared to the feed—also be combined with the bottoms product of the distillation in order to form a gasoline component. If necessary, the mixture is subjected to an additional treatment. According to a preferred embodiment of the invention, the $C_4$ hydrocarbon content of the feed is, however, deliberately kept so small that the mixture of the overhead and the bottoms products can be used as such as a component of motor fuels.

Considerable benefits are achieved by means of the invention.

As discussed above, selective hydrogenation of the olefinic hydrocarbon feedstock is achieved by the invention. The hydrogenation will reduce the amount of dienes to below 0.1% (even to below 0.05%) and also cause isomerisation of the olefins to increase the amounts of reactive olefins. The excess hydrogen and methane and other volatile compounds, if any, dispersed and dissolved in the hydrocarbon liquid phase will evaporate once the hydrogenated product stream enters the distillation column after the pre-reactors. The gas phase formed can be used for controlling the distillation.

At the same time, conducting the excess hydrogen to the distillation column removes the need for a hydrogen separation system. Were such a separation unit used to separate excess hydrogen and light hydrocarbons, some amount of light hydrocarbons would still be present in the feed. These non-condensable hydrocarbons tend to accumulate in the overhead vessel, if total condensing control scheme is used. These gases would therefore have to be purged out from the system from time to time, such purges having an effect on the pressure control and making it is difficult to keep operating pressure stable in the main fractionator. Furthermore, if light hydrocarbons were separated immediately after the selective hydrogenation the pressure would have to be lowered. This means that a pump with a spare would be needed after the separation, since hydrogenated product had to be pumped to the etherification reactors. Additional pumps increase the investment and operation costs.

An other disadvantage which is avoided by the invention is the unwanted loss of reactive components during separation operations.

The following working examples will clarify the invention:

EXAMPLE 1

A feed consisting of 55 t of FCC Light Gasoline mixed with 3 t of a Pyrolysis Gasoline cut was subjected to selective hydrogenation in a hydrogenation unit comprising a feed vessel, flow control and a fixed bed reactor unit having the configuration as shown in FIG. 2. The hydrogen feed was 20 kg/h and the gas contained about 20 kg/h of other light, inert hydrocarbons, primarily methane. The pressure of the hydrogenation was 25 bar and the temperature 90° C. The WHSV used was 6. As catalyst, a $Pd/Al_2O_3$ hydrogenation catalyst with 0,25 wt-% of palladium supplied by BASF under the tradename H 0-22, was employed.

Of the hourly feed of 20 kg $H_2$, 16 kg reacted, which means that the $H_2$ excess during hydrogenation was 20%.

Table 1 presents the results of the selective hydrogenation operation.

TABLE 1

Selective hydrogenation of an olefinic hydrocarbon feed.

| Component | Feed, wt-% | Product, wt-% |
|---|---|---|
| 3-methyl-1-butene | 0.78 | 0.15 |
| 2-methyl-1-butene | 4.13 | 2.07 |
| 2-methyl-2-butene | 7.85 | 10.45 |
| 4-methyl-1-pentene | 0.32 | 0.10 |
| 3-methyl-1-pentene | 0.48 | 0.11 |
| 2-methyl-1-pentene | 1.52 | 0.95 |
| 2-methyl-2-pentene | 1.92 | 2.81 |
| 2,3-dimethyl-1-butene | 0.51 | 0.30 |
| 2,3-dimethyl-2-butene | 0.59 | 0.70 |
| 2-ethyl-1-butene | 0.53 | 0.21 |
| 4-methyl-1-hexene | 0.06 | 0.02 |
| 3-methyl-1-hexene | 0.05 | 0.00 |
| 2-methyl-2-hexene | 0.12 | 0.18 |
| 2,3-dimethyl-1-pentene | 0.11 | 0.07 |
| 2,3-dimethyl-2-pentene | 0.05 | 0.06 |
| 2,4-dimethyl-1-pentene | 0.06 | 0.03 |
| 2-ethyl-1-pentene | 0.08 | 0.02 |
| 2-ethyl-2-pentene | 0.07 | 0.13 |
| Diolefins | 0.70 | 0.05 |

It can be seen from Table 1 that the amount of diolefins is radically reduced to 0.05% and, furthermore, that the catalyst is capable of isomerizing some non-reactive components to reactive components.

EXAMPLE 2

A feed consisting of 55 t of FCC Light Gasoline mixed with 3 t of a Pyrolysis Gasoline cut was subjected to selective hydrogenation as described in Example 1 and then to etherification in the etherification plant depicted in FIG. 3.

Table 2 shows the component flow rates before and after the selective hydrogenation unit. Also the composition of the etherification product is shown.

TABLE 2

Flow rates of hydrocarbon feed components before and after selective hydrogenation and etherification

| Stream | Feed to selective hydrogenation, kg/h | Product from selective hydrogenation, kg/h | Bottoms product of the main fractionator, kg/h |
|---|---|---|---|
| $C_4$ hydrocarbons | 1,230.0 | 1,230.0 | 116.4 |
| 3-Me-1-Butene | 351.3 | 105.4 | 99.5 |
| 2-Me-1-Butene | 2,590.0 | 1,050.0 | 49.9 |
| 2-Me-2-Butene | 5,000.0 | 6,800.0 | 933.0 |
| Remaining $C_5$'s | 18,900.0 | 18,900.0 | 18,800.0 |
| Reactive alfa $C_6$'s | 2,490.0 | 1,250.0 | 435.0 |
| Reactive beta $C_6$'s | 4,080.0 | 5,320.0 | 3,110.0 |
| Remaining $C_{6+}$ | 23,500.0 | 23,500.0 | 23,500.0 |
| Methanol | 0.0 | 0.0 | 1.1 |
| Hydrogen | 10.2 | 4.1 | 0.0 |
| TAME | 0.0 | 0.0 | 9,930.0 |
| Heavier ethers | 0.0 | 0.0 | 4,180.0 |
| Mass flow, t/h | 58.2 | 58.2 | 61.2 |
| Volume flow, $m^3/h$ | 95.7 | 97.0 | 104.2 |
| Density, $kg/m^3$ | 607.9 | 599.5 | 587.4 |
| Temperature, °C. | 60.0 | 68.0 | 106.9 |
| Pressure, kPa (abs) | 2,040.0 | 2,000.0 | 530.0 |

The composition of the distillate continuously removed during the operation of the distillation column was: 20 mol-% (1 wt-%) $H_2$, 13 mol-% (5 wt-%) methane, 4 mol-% (3 wt-%) methanol and 63 mol-% (91 wt-%) $C_4$-hydrocarbons. There are a number of other light components which will flow together with the hydrogen.

At a pressure of 500 kPa (abs.) the flow of the gaseous distillate is about 41 $m^3/h$. With a gas flow of this size, it is easy to control the pressure of the distillation column. The afore-mentioned components all behave like ideal gases. This means that their relative volume corresponds to their molar fraction, i.e. hydrogen makes up 20% of the total volume of the distillate. Together with the light hydrocarbons, the gas used for selective hydrogenation and conducted to the distillation for control of the distillate composition, makes up one third of the gaseous distillate. Such an additional amount of volatile components in the gas-phase strongly improves the possibilities of controlling the operation of the distillation.

We claim:

1. A process for preparing tertiary alkyl ethers, comprising the steps of contacting in the presence of a catalyst a feedstock containing saturated and mono- and multi-unsaturated hydrocarbons having 4 to 7 carbon atoms with an excess amount of hydrogen in relation to the multi-unsaturated hydrocarbons in order selectively to hydrogenate at least a part of the multi-unsaturated hydrocarbons to form a modified hydrocarbon feedstock, the unsaturated hydrocarbons of which are primarily comprised of mono-unsaturated compounds, feeding the modified hydrocarbon feedstock together with at least a part of the unreacted hydrogen to a catalytic distillation reactor system which includes at least one distillation column, reacting the $C_{4-7}$ isoolefines of the feedstock with an alkanol in the presence of a catalyst to form tertiary alkyl ethers, subjecting the reaction mixture to distillation in the distillation column, recovering the alkyl ethers and substantially all of the unreacted hydrocarbons with the bottoms product of the distillation, withdrawing an overhead product of the distillation, which mainly contains an azeotrope of $C_4$ hydrocarbons and the alkanol, and maintaining the pressure of the distillation column essentially constant by adjusting the amount of gaseous distillate containing hydrogen in the column.

2. The process according to claim 1, wherein a 1.001- to 10-fold molar excess of hydrogen, calculated on basis of the multi-unsaturated hydrocarbons of the feedstock, is used for hydrogenation of the hydrocarbon feedstock.

3. The process according to claim 1, wherein the hydrogenation is carried out at a sufficiently high pressure to dissolve at least 80% of the hydrogen in the hydrocarbon feedstock during hydrogenation.

4. The process according to claim 3, wherein the hydrogenation is carried out at a pressure of 15 to 115 bar.

5. The process according to claim 3, wherein the distillation is carried out at an essentially lower pressure than the hydrogenation to keep hydrogen in the gas phase during distillation.

6. The process according to claim 1, wherein the hydrogenation is carried out in the presence of a catalyst selected from the group consisting of supported noble metal catalysts and supported nickel catalysts.

7. The process according to claim 6, wherein the hydrogenation is carried out in the presence of catalyst comprising palladium on alumina, the palladium concentration of which is 0.2 to 5 wt-% calculated on basis of the total weight of the catalyst.

8. The process according to claim 1, wherein the temperature of hydrogenation is increased from about 40° C. to about 130° C. during operation in order to compensate for catalyst contamination.

9. The process according to claim 1, wherein the hydrogenation is carried out in two or more successive reactors.

10. The process according to claim 1, wherein the hydrogenation is carried out by using pure hydrogen gas.

11. The process according to claim 1, wherein the hydrogenation is carried out by using hydrogen gas containing 10 to 70 wt-% volatile light paraffins.

12. The process according to claim 1, wherein an excess at least 5 mol-% of hydrogen is fed into the hydrogenation process, the pressure of the hydrogenation process is kept at 15 bar or higher and the pressure of the distillation is kept at 10 bar or lower.

13. The process according to claim 1, wherein the alkanol comprises methanol or ethanol.

14. The process according to claim 1, wherein the amount of distillate withdrawn from the distillation corresponds at least approximately to the amount of $C_4$ hydrocarbons present in the feed.

* * * * *

UNITED STATES PATENT AND TRADEMARK OFFICE
CERTIFICATE OF CORRECTION

PATENT NO. : 5,689,013
DATED : November 18, 1997
INVENTOR(S) : Jarvelin et al.

It is certified that error appears in the above-identified patent and that said Letters Patent is hereby corrected as shown below:

Amend the Assignee as follows:

--NESTE OY, Espoo, Finland--

Signed and Sealed this

Twenty-third Day of June, 1998

Attest:

BRUCE LEHMAN

*Attesting Officer*     *Commissioner of Patents and Trademarks*